United States Patent [19]

Drake et al.

[11] 4,215,019

[45] Jul. 29, 1980

[54] RUTHENIUM-COBALT-GOLD CATALYST FOR HYDROGENATION OF UNSATURATED DINITRILES

[75] Inventors: Charles A. Drake; Timothy P. Murtha, both of Bartlesville, Okla.

[73] Assignee: Phillips Petroleum Company, Bartlesville, Okla.

[21] Appl. No.: 960,798

[22] Filed: Nov. 14, 1978

[51] Int. Cl.$^2$ .................. B01J 21/04; B01J 23/46; B01J 23/52; B01J 23/74

[52] U.S. Cl. .............................. 252/466 B; 252/472; 260/583 K

[58] Field of Search ............................ 252/466 B, 472; 260/583 K

[56] References Cited

U.S. PATENT DOCUMENTS

| | | | |
|---|---|---|---|
| 3,859,342 | 1/1975 | Fukumi et al. | 260/518 R |
| 3,880,929 | 4/1975 | Drake | 260/583 P |
| 4,003,933 | 1/1977 | Drake | 260/583 K |
| 4,140,720 | 2/1979 | Drake | 252/472 X |

*Primary Examiner*—W. J. Shine

[57] ABSTRACT

Cobalt and gold in a ruthenium hydrogenation catalyst markedly increases the yield of product. A method for hydrogenating branched-chain olefinically unsaturated aliphatic dinitrile employing a ruthenium-cobalt-gold catalyst to produce saturated diamines is set forth.

6 Claims, No Drawings

RUTHENIUM-COBALT-GOLD CATALYST FOR HYDROGENATION OF UNSATURATED DINITRILES

This invention relates to hydrogenation. In one of its aspects it relates to a novel catalyst suited for hydrogenation processes. In another of its aspects the invention relates to a method for the hydrogenation of organic compounds. In one of its specific aspects the invention relates to the hydrogenation of branched-chain olefinically unsaturated aliphatic dinitriles.

In one of its concepts the invention provides a process for the hydrogenation of an olefinically unsaturated dinitrile, e.g., a dinitrile derived from the reaction of isobutylene and acrylonitrile. In another of its concepts the invention provides such a method for the hydrogenation of a mixture of olefinically unsaturated dinitriles obtained from a reaction of isobutylene and acrylonitrile, as known in the art. In a further concept of the invention it provides a catalyst, especially suited for the process herein described, the catalyst comprising essentially ruthenium, cobalt, and gold. The catalyst is generally employed employing a support, e.g., gamma-alumina. In a further concept of the invention it provides a method for preparing the herein described catalyst by contacting a suitable support, e.g., gamma-alumina support, with an aqueous solution of a soluble ruthenium salt, e.g., ruthenium trichloride, a soluble cobalt salt or compound, e.g., cobalt(II) chloride, and a soluble gold salt, e.g., hydrogen tetrachloroaurate(III), drying the thus impregnated support, preferably at reduced pressure and at a temperature not in substantial excess over 125° C. and then reducing the thus obtained mass in the presence of hydrogen.

The hydrogenation of compounds of all kinds under hydrogenation conditions and in the presence of suitable catalysts is a well-worked art. Yet, there appears to be considerable room for improvement. Especially is this so in many instances in which long time runs for hydrogenation with a catalyst are sought to be improved.

We have now discovered that by combining cobalt and gold in a ruthenium hydrogenation catalyst there can be obtained, quite surprisingly, a very large increase in yield of hydrogenated product. This is especially the more surprising that a ruthenium-gold catalyst, not containing cobalt, functioned considerably less well than did a ruthenium-cobalt catalyst or even a catalyst having only ruthenium therein, all as evidenced by the experimental data given herein.

The invention will now be described as it relates to the hydrogenation of a branched-chain olefinically unsaturated aliphatic dinitrile, e.g., as present in a mixture obtained from the reaction of isobutylene and acrylonitrile, known in the art.

It is an object of this invention to provide a process for the hydrogenation of a compound. It is another object of the invention to provide a catalyst suited for the hydrogenation of a compound. It is a further object of the invention to provide a process for the hydrogenation in an improved manner of a branched-chain olefinically unsaturated dinitrile. It is a still further object of the invention to provide a process for the improved hydrogenation of a mixture of branched-chain olefinically unsaturated aliphatic dinitriles obtained from a reaction of isobutylene and acrylonitrile. Another object of the invention is to provide an improved ruthenium hydrogenation catalyst.

Other aspects, concepts, objects and the several advantages of the invention are apparent from a study of this disclosure and the appended claims.

According to the present invention, as unsaturated compound, e.g., an unsaturated aliphatic dinitrile, for example, a branched-chain unsaturated aliphatic dinitrile, which can be derived from a reaction of isobutylene and acrylonitrile, is advantageously and efficiently hydrogenated, under hydrogenation conditions, with a catalyst essentially comprising ruthenium, cobalt and gold, generally impregnated upon a suitable support, e.g., gamma-alumina.

Also according to the present invention there is provided a novel hydrogenation catalyst, suited for the hydrogenations herein mentioned, the catalyst comprising essentially ruthenium, cobalt and gold, generally disposed upon a suitable support or contact mass.

More specifically, in a now preferred embodiment, the invention provides a process for the catalytic hydrogenation of branched-chain olefinically unsaturated aliphatic dinitriles in the presence of ammonia, hydrogen, a diluent, a catalyst consisting of a first component selected from elemental ruthenium, compounds of ruthenium which are reducible by hydrogen to elemental ruthenium, and mixtures thereof and a second component selected from elemental cobalt, compounds of cobalt reducible by hydrogen to elemental cobalt, and mixtures thereof, and a promoter consisting of elemental gold, compounds of gold, and mixtures thereof.

The branched-chain unsaturated aliphatic dinitriles which are advantageously and efficiently hydrogenated in accordance with the process of this invention are the unsaturated dinitriles of the formula:

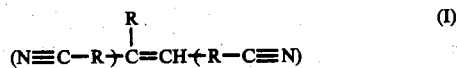

wherein each R is independently selected from the group consisting of an alkylene radical and an alkylidene radical and R' is an alkyl radical. Each R and R' will generally have from one to fifteen carbon atoms, preferably from one to six, and more preferably from one to three carbon atoms. In general, the unsaturated dinitrile reactant of formula (I) will contain from seven to 30 carbon atoms, preferably from eight to 16 carbon atoms, and more preferably from nine to 12 carbon atoms.

Representative of unsaturated reactant species of formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures thereof.

If desired, other unsaturated dinitrile reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula:

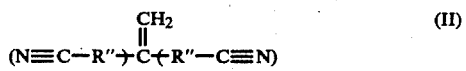

(II)

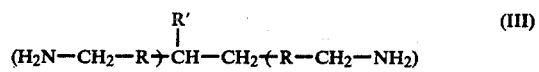

(III)

wherein each R″ is independently selected from the group consisting of an alkylene radical and an alkylidene radical. In general, each R″ will have from one to 15 carbon atoms, preferably from one to seven carbon atoms, and more preferably from one to four carbon atoms. The dinitriles of formula (II) will generally contain from six to 30 carbon atoms, preferably from eight to 16 carbon atoms, and more preferably from nine to 12 carbon atoms.

Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the invention increase with increasing concentrations of the dinitriles of formulas (I) in the feedstock. Thus, the process of the invention is even more advantageous for concentrations of the dinitriles of formula (I) in the feedstock of at least 5 weight percent. The invention is considered to be particularly advantageous for dinitrile feedstocks having a concentration of the dinitriles of formula (I) of at least 10 weight percent.

A presently preferred branched-chain unsaturated aliphatic dinitrile feedstock for employment in the practice of this invention is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

In the practice of this invention, the catalyst hydrogenation of the unsaturated dinitrile reactant of formula (I) results primarily in the formation of saturated diamine reaction products having the formula:

wherein R and R′ are as previously defined.

The catalytic hydrogenation of an unsaturated dinitrile reactant of formula (II) results primarily in the formulation of saturated diamine reaction products having the formula:

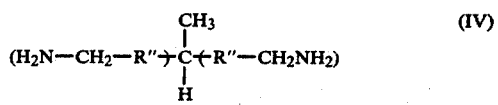

(IV)

wherein R″ is as previously defined.

Materials that are considered to be suitable for use as the first catalyst component in the gold-promoted hydrogenation catalyst of this invention include finely divided elemental ruthenium, compounds of ruthenium which are reducible by hydrogen to finely divided elemental ruthenium and mixtures thereof. Suitable reducible compounds include the oxides, halides, nitrates, oxalates, acetates, carbamates, propionates, tartrates, hydroxides, and the like and mixtures thereof. Specific examples include elemental ruthenium, ruthenium dioxide, ruthenium tetraoxide, ruthenium trichloride, ruthenium tetrachloride, ruthenium trinitrate, ruthenium triacetate, ruthenium(III) carbonate, ruthenium trihydroxide, and the like and mixtures thereof.

Materials that are considered to be suitable for use as the second catalyst component in the gold-promoted catalyst of this invention include finely divided elemental cobalt, compounds of cobalt which are reducible by hydrogen to finely divided elemental cobalt, and mixtures thereof. Suitable reducible compounds include the oxides, halides, nitrates, oxalates, acetates, carbamates, propionates, tartrates, hydroxides, and the like, and mixtures thereof. Specific examples include cobalt(II) acetate, cobalt(III) acetate, cobalt(II) benzoate, cobalt(II) bromide, cobalt(II) chloride, cobalt(III) chloride, cobalt(II) hydroxide, cobalt(III) hydroxide, cobalt(II) nitrate, cobalt(II) oxide, cobalt(III) oxide, cobalt(II) oxalate, and the like, and mixtures thereof.

The amount of the second component will generally be in the range from about 10 to about 300 weight percent, and preferably will be in the range from about 20 to about 200 weight percent, calculated as the element, based on the weight of the first component in the catalyst. Herein and in the claims amounts or percentages, unless otherwise qualified, are of the metals, calculated as the element.

The weight ratio of the catalyst to unsaturated dinitrile reactant in a batch reaction, based on the weight of the component metal contained therein, can be varied as desired. For the purpose of maintaining reasonable reaction rates under economically attractive catalytic reaction kinetics, it is generally preferred in a batch reaction that the weight ratio of the first component to the unsaturated dinitrile reactants be maintained within a range of about 0.01:100 to about 30:100, and preferably in the range of about 0.1:100 to about 20:100.

The promoter used in the practice of this invention is selected from elemental gold, compounds of gold, and mixtures thereof. Specific examples of promoters include elemental gold, gold(I) bromide, gold(III) bromide, gold(I) chloride, gold(III) chloride, gold(III)

oxide, hydrogen tetrachloroaurate(III) (HAuCl₄), and the like and mixtures thereof. The amount of gold promoter, calculated as elemental gold, utilized will be in the range from about 5 to about 200 weight percent, preferably from about 10 to about 100 weight percent based on the ruthenium content in the catalyst. When a support is employed in a batch process, the elemental ruthenium content will generally be in the range of about 0.5 to about 50 weight percent, preferably in the range of about 1 to about 10 weight percent, based on the weight of the support. When a support is employed in a continuous process, the elemental ruthenium content will generally be in the range of about 0.01 to about 10 weight percent, preferably in the range of about 0.05 to about 5 weight percent, based on the weight of the support.

In the practice of this invention, it is often desirable to employ catalytic amounts of the first catalyst component, the second catalyst component, and the promoter supported by a solid catalyst carrier which does not deleteriously affect the catalytic hydrogenation process of this invention. Such supports include, for example, carbon, kieselguhr, silica, alumina, silica-alumina, calcium carbonate, barium carbonate, asbestos, pumice, clays, and the like, and mixtures thereof. The support can be in the form of tablets, pellets, extrudates, granules, and the like and mixtures thereof. The first catalyst component, the second catalyst component, and the promoter can be added to the catalyst support by any of the methods well known in the art. For example, the supported catalysts can be prepared by dry mixing the components or by impregnating the support with a solution or dispersion of ruthenium and cobalt in elemental form or in the form of reducible compounds thereof, and elemental gold or compounds of gold.

The supported catalyst can be pretreated with hydrogen or other reducing agents known in the art to reduce the compounds, or such reduction can be achieved in the hydrogenation reactor.

Generally speaking, one skilled in this art in possession of this disclosure, having studied the same, will be able to apply its concepts to prepare a catalyst suited to his purpose including the determination of the respective proportions of the catalytic ingredients and/or support, the basic concept of the catalyst invention being in the discovery that gold somehow considerably and surprisingly improves the basic ruthenium containing catalyst even when cobalt is present therein.

Any catalytic hydrogenation temperature can be employed which provides the desired degree of catalytic efficiency in the hydrogenation of the branched-chain unsaturated aliphatic dinitrile containing feedstock. The hydrogenation temperatures will generally be within the range of about 40° to about 250° C., preferably within the range of about 80° to about 225° C., and more preferably within the range of about 100° to about 200° C.

The catalytic hydrogenation of branched-chain unsaturated aliphatic dinitriles can be carried out at any hydrogen pressure wherein both the olefinic unsaturation and the nitrile groups are reduced in the presence of ammonia, hydrogen and a suitable diluent. Generally, suitable hydrogen pressures are within the range of from about 100 to about 5,000 psig, but lower or even higher hydrogen pressures can be employed. Preferably, due to economic considerations, hydrogen pressures within the range of about 500 to about 3,000 psig are employed. Higher hydrogen pressures may be desirable at lower reaction temperatures in order to achieve complete reduction within a reasonable reaction time.

Any time interval suited for the catalytic hydrogenation of branched-chain unsaturated aliphatic dinitriles can be employed in the practice of this invention. However, time intervals economically attractive to the process are generally within the range of about 15 minutes to about 5 hours for a batch hydrogenation process. A reaction time in the range of about 1 to about 3 hours is presently preferred in order to insure substantially complete hydrogenation of any unsaturated olefinic bonds in the feedstock as well as complete hydrogenation of the nitrile groups to primary amino groups. The catalytic hydrogenation of unsaturated dinitriles in accordance with the process of this invention can be carried out as a continuous process at any suitable liquid hourly space velocity (LHSV). However, the liquid hourly space velocity rates will generally be within the range of about 0.1 to about 20, more preferably from about 0.5 to about 10, volumes of unsaturated dinitrile reactant plus diluent and ammonia per volume of catalyst (including the volume of any catalyst support if any is present) per hour.

While any suitable diluent can be employed in the process of this invention, the diluent will generally be selected from the class consisting of unsubstituted tertiary alkanols containing from 4 to 12 carbon atoms per molecule, unsubstituted acyclic and unsubstituted cyclic ethers having from 4 to 12 carbon atoms per molecule, and saturated hydrocarbons having 4 to 12 carbon atoms per molecule, and mixtures thereof. The term "unsubstituted" signifies that there are no substituents other than hydrocarbyl radicals. Examples of suitable tertiary alkanol diluents include 2-methyl-2-propanol, 2-methyl-2-butanol, 3-ethyl-3-hexanol, 3-ethyl-3-pentanol, 3,7-dimethyl-3-octanol, 3-ethyl-3-decanol, and the like, and mixtures thereof. Examples of alkanes and cycloalkanes include butane, pentane, hexane, decane, dodecane, cyclobutane, cyclopentane, cyclohexane, cyclodecane, cyclododecane, 2-methylbutane, methylcyclopentane, 2,2,4-trimethylpentane, and mixtures thereof. Examples of ethers include 1,3-dioxane, 1,4-dioxane, tetrahydrofuran, 4,4-dimethyl-1,3-dioxane, and mixtures thereof. To facilitate handling of the reaction mixtures, the weight ratio of unsaturated dinitrile reactants to diluent charged to the reaction zone is generally within the weight ratio range of about 0.001:100 to about 35:100, and is preferably in the range of about 0.1:100 to about 25:100.

A secondary amine formation suppressant, preferably ammonia, is employed in the process of this invention as a means of suppressing undesirable side reactions such as the formation of secondary and tertiary amines. Any amount of secondary amine formation suppressant can be employed which is effective in deterring or reducing undesirable side reactions. In general, the mole ratio of secondary amine formation suppressant to cyano group (there being two cyano groups in each unsaturated dinitrile) will be in the range 1:1 to about 25:1, and preferably will be in the range of about 3:1 to about 20:1. The absence of a suppressant would yield inferior results. However, with gold in the catalyst these results would show improvement over a catalyst not containing it.

Recovery of the desired end product, the branched-chain saturated aliphatic diamines, as well as any resulting reaction byproducts, any unconsumed reactants, ammonia, hydrogen, and/or diluents can be carried out by any conventional separation means. In general, at the conclusion of the catalytic hydrogenation process in a batch process, the reaction zone effluent is cooled and depressurized with the recovery, if desired, of any ammonia or diluent which is vented from the reaction zone effluent during the depressurizing operation. The ammonia or diluent can be returned or recycled to the hydrogenation zone if desired. The reaction products can be separated from the catalyst by conventional filtration means. The filtrate containing the saturated diamines can be conveniently separated from any reaction byproducts or any diluent remaining in the filtrate by any conventional fractional distillation.

In a continuous process, the reactor effluent is depressured and the diluent and ammonia removed by distillation. The recovered diluent and ammonia can be recycled to the hydrogenation zone, if desired. The saturated diamines can be separated from any reaction byproducts or any remaining diluent by any conventional fractional distillation.

The saturated diamine products of this invention are useful in the preparation of polymers. Of particular interest are the polyamides. The terephthalamide polymers have been found to be of value for the production of fibers and engineering plastics.

EXAMPLES

The starting material in each of the runs in this example is a mixture of olefinically unsaturated dinitriles prepared by the reaction of isobutylene and acrylonitrile. This reaction mixture contains approximately 52 weight percent 5-methylenenonanedinitrile, approximately 35 weight percent 5-methyl-4-nonenedinitrile, approximately 12 weight percent of the combination of 2,4-dimethyl-4-octenedinitrile, 2-methyl-4-methyleneoctanedinitrile, and 2,4-dimethyl-3-octenedinitrile, and approximately 1 weight percent of the combination of 2,6-dimethyl-4-methyleneheptanedinitrile, and 2,4,6-trimethyl-3-heptenedinitrile. For simplicity, the above described reaction mixture will be called diadduct. Hydrogenation of both the olefinic and nitrile unsaturation of diadduct yields a saturated diamine mixture.

In each hydrogenation run, a 0.5" (12.7 mm) diameter × 20" (508 mm) length continuous reactor fitted with a steam heating system and temperature recorder was charged with 20 g. of the supported catalyst, flushed with nitrogen, flushed with hydrogen at a rate of 1 liter per minute, and heated to 140° C. A mixture containing diadduct, 2-methyl-2-propanol, and ammonia in a weight ratio of 1/8/1 was fed to the reactor at a LHSV of about 6. The reactor conditions during the hydrogenation runs were 1500 psig (10.3 MPa) pressure, 140° C., and 1 liter per minute hydrogen flow.

Samples were collected from the reactor effluent after 4 hours of run time and after 19 hours of run time and were analyzed by vapor phase chromatography after removal of the 2-methyl-2-propanol and ammonia under reduced pressure.

The supported catalysts were prepared by contacting a commercial gamma-alumina support with an aqueous solution of the metal chloride(s) [ruthenium trichloride, cobalt(II) chloride, hydrogen tetrachloroaurate(III)] overnight and then removing the water in a rotary evaporator with reduced pressure. The impregnated support was dried at 125° C. under reduced pressure (about 10 mm mercury) overnight and reduced in the presence of hydrogen at 300° C. for 3 hours.

Four hydrogenation runs were carried out in which diadduct was hydrogenated in the presence of various catalysts. The catalyst in run 1 contained 0.5 weight % ruthenium and the catalyst in run 2 contained 0.5 weight % ruthenium and 0.5 weight % cobalt. Run 3 utilized a catalyst which contained 0.5 weight % ruthenium and 0.25 weight % gold. Run 4 was carried out according to the present invention and utilized a catalyst containing 0.5 weight % ruthenium, 0.5 weight % cobalt, and 0.25 weight % gold. Each percentage is based on the weight of the support. The results of these runs are presented in Table I.

TABLE I

| Run No. | Catalyst Composition[a] | | | Saturated Diamines,[b] Weight % | |
|---|---|---|---|---|---|
| | Ruthenium Weight % | Cobalt, Weight % | Gold, Weight % | 4 hours | 19 hours |
| 1 | 0.5 | 0 | 0 | 67 | 32 |
| 2 | 0.5 | 0.5 | 0 | 80 | 69 |
| 3 | 0.5 | 0 | 0.25 | 53 | [c] |
| 4 | 0.5 | 0.5 | 0.25 | 97 | 78 |

[a]Weight % metal based on the weight of the support.
[b]Weight % saturated diamines in the reaction product at the indicated number of hours in the run. The % is calculated based on the total product weight after removal of the diluent and ammonia.
[c]Very little product formed.

The results presented in Table I show that a run 4, using a catalyst containing ruthenium, cobalt, and gold, resulted in a much higher level of the desired saturated diamine product than control run 1, using ruthenium only, run 2 using ruthenium and cobalt, or run 3 using ruthenium and gold. The results of run 4 are considered surprising in view of the results of run 3 in which gold appears to be detrimental to a ruthenium catalyst in the absence of cobalt.

It appears reasonable, in view of the data, to conclude that nitrile and other unsaturation hydrogenation or saturation of unsaturation in carbon to carbon bonding will be improved with the novel catalyst described herein. This is especially so since it is known that dinitriles present more difficulty in their hydrogenation than most other organics of similar, but not identical, structure.

Reasonable variation and modification are possible within the scope of the foregoing disclosure and the appended claims to the invention the essence of which is that the use of gold to modify a ruthenium catalyst, also containing cobalt, has been found to materially improve hydrogenation activity, especially as applied to dinitriles described herein and that, therefore, a method for the hydrogenation of organic materials, especially dinitriles, also as described herein, has been set forth.

We claim:

1. A catalyst suited for hydrogenation of compounds essentially comprising ruthenium, cobalt and gold.

2. A catalyst according to claim 1 wherein minor amounts of said elements are composited with a suitable support.

3. A catalyst according to claim 1 wherein the elements are composited with an alumina support.

4. A catalyst according to claim 3 wherein the support is gamma-alumina.

5. A catalyst according to claim 1 wherein a batch operation is effected and a support is employed, the elemental ruthenium content is in the range of from about 0.5 to about 50 weight percent, the cobalt is present in the approximate range of from about 10 to about 300 weight percent based on the weight of the ruthenium in the catalyst, and the gold is present in the approximate range of from about 5 to about 200 weight percent, also based on the ruthenium content of the catalyst.

6. A catalyst according to claim 1 wherein a continuous operation is effected and a support is employed, the elemental ruthenium content is in the range of from about 0.01 to about 10 weight percent, the cobalt is present in the approximate range of from about 10 to about 300 weight percent based on the weight of the ruthenium in the catalyst, and the gold is present in the approximate range of from about 5 to about 200 weight percent, also based on the ruthenium content of the catalyst.

* * * * *